United States Patent [19]

Ozaki et al.

[11] 4,376,119

[45] Mar. 8, 1983

[54] BENZOTHIAZINE DERIVATIVE

[75] Inventors: Shoichiro Ozaki; Hideya Kobayashi, both of Kamakura; Haruki Mori, Yokohama; Hiroshi Kawazura, Mobara; Yutaka Okazaki, Mobara; Takafumi Kitano, Mobara; Mikio Kumakura, Mobara; Takuo Nakano, Yokohama, all of Japan

[73] Assignee: Mitsui Toatsu Chemicals, Inc., Tokyo, Japan

[21] Appl. No.: 274,209

[22] Filed: Jun. 16, 1981

[30] Foreign Application Priority Data

Feb. 24, 1981 [JP] Japan .................................. 56/25002

[51] Int. Cl.³ ..................... A61K 31/54; C07D 417/12
[52] U.S. Cl. ..................................... 424/246; 544/49
[58] Field of Search ........................... 544/49; 424/246

[56] References Cited

U.S. PATENT DOCUMENTS 3,591,584  7/1971  Lombardino ........................ 260/243
3,853,862 12/1974  Lombardino ........................ 544/49
3,892,740  7/1975  Lombardino ........................ 544/49
4,116,964  9/1978  Zinnes et al. ....................... 544/49

FOREIGN PATENT DOCUMENTS 47-29373 11/1972 Japan .

Primary Examiner—John M. Ford
Attorney, Agent, or Firm—Fisher, Christen & Sabol

[57] ABSTRACT

N-(6-fluoro-2-pyridyl)-3,4-dihydro-2-methyl-4-oxo-2H-1,2-benzothiazine-3-carboxamide 1,1-dioxide that is a novel benzothiazine derivative. The compound is characterized by a low degree of toxicity and a low incidence of gastric disorders and useful as an anti-inflammatory agent.

2 Claims, No Drawings

BENZOTHIAZINE DERIVATIVE

BACKGROUND OF THE INVENTION

(1) Field of the Invention

This invention relates to a novel benzothiazine derivative, a process for the preparation of same, and a pharmaceutical composition (in particular, an anti-inflammatory composition) containing same.

(2) Description of the Prior Art

In the past, aspirin, fenoprofen and the like were used as anti-inflammatory, analgesic and antipyretic agents. More recently, indomethacin, diclofenac and the like came into common use because of their high anti-inflammatory activity. However, these compounds have such disadvantages as a high degree of toxicity, a high incidence of gastric disorders, a short duration of action, and the like.

Accordingly, Piroxicam [3,4-dihydro-2-methyl-4-oxo-N-(2-pyridyl)-2H-1,2-benzothiazine-3-carboxamide 1,1-dioxide] and Sudoxicam [3,4-dihydro-2-methyl-4-oxo-N-(2-thiazolyl)-2H-1,2-benzothiazine-3-carboxamide 1,1-dioxide] have been developed as long-acting anti-inflammatory agents of the benzothiazine series (U.S. Pat. No. 3,591,584). Although these compounds have a potent and long-lasting anti-inflammatory activity, their high degree of toxicity and high incidence of gastric disorders are not appreciably different from those of indomethacin and diclofenac.

Meanwhile, Isoxicam [3,4-dihydro-2-methyl-N-(5-methyl-3-isoxazolyl)-4-oxo-2H-1,2-benzothiazine-3-carboxamide 1,1-dioxide] has also been developed as an anti-inflammatory agent (Japanese Patent Laid-Open No. 29373/'72). This compound has an isoxazole structure, so that its degree of toxicity and incidence of gastric disorders are relatively low. However, its anti-inflammatory activity is lower than that of Piroxicam and Sudoxicam.

SUMMARY OF THE INVENTION

It is an object of the present invention to provide a novel benzothiazine derivative which is characterized by a low degree of toxicity and a low incidence of gastric disorders as well as a potent and long-lasting anti-inflammatory activity.

In accordance with the present invention, there is provided an N-(6-fluoro-2-pyridyl)-3,4-dihydro-2-methyl-4-oxo-2H-1,2-benzothiazine-3-carboxamide, 1,1-dioxide of the formula

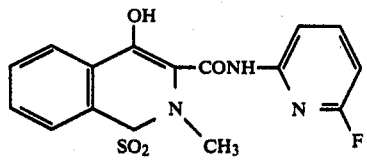

where the benzothiazine ring is, for convenience, shown in the enol form with a hydroxyl group at the 4-position but actually exhibits keto-enol tautomerisum.

The compound of formula (1) is suitable for use as an anti-inflammatory agent.

DETAILED DESCRIPTION OF THE INVENTION

The compound of formula (1) can be prepared by heating methyl 3,4-dihydro-2-methyl-4-oxo-2H-benzothiazine-3-carboxylate 1,1-dioxide (that is a well-known compound as described in J. Med. Chem., 14, 1171, 1971) and a 2-amino-6-fluoropyridine in xylene to effect condensation thereof. This reaction is preferably carried out by using the reactants in a molar ratio of 1:1 or the 2-amino-6-fluoropyridine in slight excess. Usually, the reaction temperature is of the order of 100° to 150° C. and the reaction time is in the range of 2 to 20 hours. After completion of the reaction, the reaction mixture is cooled to precipitate and crystallize the desired product. This product is separated, for example, by filtration and then washed with xylene, alcohol, chloroform or the like to obtain highly pure crystals. The structure of the desired product can be confirmed by elemental analysis, N.M.R. spectroscopy and the like.

With respect to anti-inflammatory activity, the duration thereof, the incidence of gastric disorders, and toxicity ($LD_{50}$), the compounds of formula (1) was evaluated as described in Examples 2 to 5 which will be given later. The results thus obtained are summarized in Table 1, so as to permit comparison with control drugs such as Piroxicam, Sudoxicam and Isoxicam, conventional anti-inflammatory agents such as indomethacin and diclofenac, and well-known analogous compounds such as N-(5-chloro-2-pyridyl)-3,4-dihydro-2-methyl-4-oxo-2H-1,2-benzothiazine-3-carboxamide 1,1-dioxide (hereinafter referred to as the 5-chloro-2-pyridyl compound) and N-(6-methyl-2-pyridyl)-3,4-dihydro-2-methyl-4-oxo-2H-1,2-benzothiazine-3-carboxamide 1,1-dioxide (hereinafter referred to as the 6-methyl-2-pyridyl compound).

TABLE 1

| Test Compound | Anti-inflammatory activity, $ED_{50}$ (mg/kg) | Gastric disorders, $UD_{50}$ (mg/kg) | Therapeutic index, $UD_{50}/ED_{50}$ | Acute toxicity, $LD_{50}$ (mg/kg) | Safety margin, $LD_{50}/ED_{50}$ |
|---|---|---|---|---|---|
| Compound of formula (1) | 7.5 | 297 | 39.6 | >5,000 | >667 |
| Piroxicam | 1.75 | 8.2 | 4.7 | 490 | 280 |
| Sudoxicam | 5.1 | 11.8 | 2.3 | 500 | 98 |
| Isoxicam | 15.5 | 250 | 16.1 | 5,000 | 322 |
| Indomethacin | 4.6 | 5.4 | 1.2 | 17** | 3.7 |
| Diclofenac | 5.0 | 9.2 | 1.8 | 420*** | 84 |
| 5-Chloro-2-pyridyl compound | * | — | — | — | — |
| 6-Methyl-2-Pyridyl compound | 4.5 | 5.1 | 1.1 | — | — |

*When this compound was orally administered in a dose of 6.5 mg/kg, the rate of suppression of edema was found to be as low as 18.9% (see Table 2). Accordingly, no further tests on this compound were carried out.
**This value is reported in Pharmacometrics, 6(6), 1285 (1972).
***This value is reported in Folia Pharmacologica Japonica, 69, 319 (1973).

As can be seen from the data given in Table 1, the benzothiazine derivatives including the compound of formula (1), Piroxicam, Sudoxicam and Isoxicam are all superior in therapeutic index and safety margin to indomethacin and diclofenac. Among others, the therapeutic index and safety margin of the compound of formula (1) are remarkably high. When used in clinical applications, therefore, the compound of formula (1) are presumed to involve very little risk of producing such side effects (i.e., gastric disorders) as occur frequently as a result of administration of non-steroidal anti-inflammatory agents. Moreover, the compound of formula (1) is excellent in the duration of anti-inflammatory activity as is evident from Table 3 given in Example 3.

It may be understood from the above description that the compound of formula (1) has not only a potent and long-lasting anti-inflammatory activity but also a very high degree of safety.

Depending on the type of symptoms and their sites of manifestation, the compound of formula (1) can be administered in a variety of dosage forms, for example, oral preparations such as tablets, capsules, powders, granules, etc.; suppositories; liquid preparations; ointments; injectable solutions for intravenous intramuscular and other injection purposes; and the like. However, they are preferably administered in the form of oral preparations or suppositories. Their daily doses for adults can range from 1 to 50 mg and preferably from 5 to 20 mg. Usually, it is sufficient to administer the compound of formula (1) once a day.

The pharmaceutical compositions of the present invention contain an active ingredient at a concentration of about 10 to 95% and preferably 15 to 90%. They can be prepared by any of well-known conventional techniques such as blending, granulation, sugar coating, dissolution and freeze-drying. For example, pharmaceutical compositions for oral use are prepared by combining an active ingredient with a solid carrier and adding thereto suitable additives as desired. Specifically, sugars, cellulose derivatives, calcium phosphate and the like are used as the carrier, and binders, disintegrants (such as starch), flow controllers, lubricants and the like are used as the additives. Furthermore, depending on the dosage form, any suitable materials may be incorporated into the pharmaceutical compositions of the present invention.

The present invention is further illustrated by the following examples.

EXAMPLE 1

[Preparation of N-(6-fluoro-2-pyridyl)-3,4-dihydro-2-methyl-4-oxo-2H-1,2-benzothiazine-3-carboxamide 1,1-dioxide]

(1) Synthesis of 2-amino-6-fluoropyridine

In an autoclave were placed 4.75 g of 2,6-difluoropyridine and 48 ml of a 29% aqueous ammonia solution. The resulting mixture was heated to 150° C. and stirred for 45 minutes. After the mixture was cooled by allowing it to stand overnight, the resulting precipitate was separated by filtration and washed with ice water. Then, the precipitate was dissolved in 50 ml of dichloromethane and the resulting solution was washed with 40 ml of water. The dichloromethane layer was dried over anhydrous sodium sulfate and then concentrated to dryness. The resulting residue was recrystallized from chloroform-petroleum ether. Thus, 3.4 g of crystals having a melting point of 56°-58° C. were obtained in a 75% yield.

(2) Synthesis of N-(6-fluoro-2-pyridyl)-3,4-dihydro-2-methyl-4-oxo-2H-1,2-benzothiazine-3-carboxamide 1,1-dioxide A mixture consisting of 7.68 g (0.0285 mole) of methyl 3,4-dihydro-2-methyl-4-oxo-2H-benzothiazine-3-carboxylate 1,1-dioxide, 4.8 g (0.0428 mole) of 2-amino-6-fluoropyridine, and 29 ml of xylene was refluxed for 17 hours, during which the methanol formed by this reaction was continuously distilled off. After the mixture was cooled by allowing it to stand overnight, the resulting precipitate was separated by filtration. The filtrate was concentrated and then cooled to obtain an additional precipitate, which was combined with the previously obtained precipitate and washed with hot chloroform. Thus, 7.2 g of crystals having a melting point of 246°-248° C. (decomp.) were obtained in a 72.3% yield.

Elemental analysis—Calc.d for $C_{15}H_{12}FN_3O_4S$ (mol. wt. 349.35): C, 51.55; H, 3.46; F, 5.44; N, 12.03; S, 9.18. Found: C, 51.69; H, 3.23; F, 5.55; N, 12.29; S, 9.14.

N.M.R. spectrum (DMSO-$d_6$ solvent)—$\delta=2.87$ (3H, s, N—CH$_3$), 6.92-7.1 and 7.85-8.2 (7H, m, $C_6H_4$ and $C_5H_3N$), 10.70 (1H, broad OH).

EXAMPLE 2

Anti-inflammatory activity was tested as follows: Male rats of the Wistar strain were used in groups of 7. A test compound was suspended in a 0.2% carboxymethyl cellulose solution and orally administered in a dose of 0.5 ml/100 g of body weight. One hour after administration of the test compound, 0.1 ml of a 1% solution of carrageenin (which is known to be capable of causing inflammation) was subcutaneously injected into the sole of the right hind leg of each rat. Three hours after injection of carrageenin, each rat was sacrificed by ether. The feet of both hind legs were amputated at the ankle joint and weighed to detect the difference in weight between both feet. Then, the ability of the test compound to suppress the carrageenin-induced edema was evaluated by comparing the foot weight difference of the test group with that of a control group (consisting of rats to which the solvent alone was administered). Specifically, the rate of suppression of the edema was calculated according to the following equation:

Rate of Suppression of Edema (%) =

$$\frac{[\text{Foot Weight Difference (g) of Control Group}] - [\text{Foot Weight Difference (g) of Test Group}]}{[\text{Foot Weight Difference (g) of Control Group}]} \times 100$$

The results thus obtained are shown in Table 2.

TABLE 2

| Test Compound | Dose (mg/kg, p.o.) | Rate of Suppression of Edema (%) | Dose Producing 50% Suppression, ED$_{50}$ (mg/kg, p.o.) |
|---|---|---|---|
| Compound of formula (1) | 2.0 | 20.0 | 7.5 |
| | 4.0 | 32.0 | |
| | 8.0 | 54.6 | |
| | 16.0 | 66.6 | |
| Piroxicam | 0.625 | 26.9 | 1.75 |
| | 1.25 | 42.5 | |
| | 2.5 | 57.0 | |
| | 5.0 | 76.4 | |
| Sudoxicam | 1.25 | 14.9 | 5.1 |
| | 2.5 | 30.7 | |
| | 5.0 | 45.5 | |
| | 10.0 | 69.3 | |
| Isoxicam | 3.75 | 7.5 | 15.5 |
| | 7.5 | 32.3 | |
| | 15.0 | 46.8 | |
| | 30.0 | 69.4 | |
| Indomethacin | 1.25 | 19.3 | 4.6 |
| | 2.5 | 22.8 | |
| | 5.0 | 57.4 | |
| | 10.0 | 73.3 | |
| Diclofenac | 2.5 | 29.7 | 5.0 |
| | 5.0 | 48.5 | |
| | 10.0 | 69.3 | |
| 5-Chloro-2-pyridyl | 6.5 | 18.9 | — |

TABLE 2-continued

| Test Compound | Dose (mg/kg, p.o.) | Rate of Suppression of Edema (%) | Dose Producing 50% Suppression, ED$_{50}$ (mg/kg, p.o.) |
|---|---|---|---|
| 6-Methyl-2-pyridyl compound | 1.75 | 27.4 | 4.5 |
| | 6.5 | 58.9 | |

EXAMPLE 3

The duration of anti-inflammatory activity was tested as follows: Employing the ED$_{50}$ values determined in Example 3, the duration of anti-inflammatory activity was examined by varying the premedication time. The premedication time was defined as the time interval between the administration of a test compound and the injection of carrageenin. Tests were carried out in substantially the same manner as described in Example 2. The results thus obtained are shown in Table 3.

TABLE 3

| Test Compound | Rate of Suppression of Edema (%) in Rats Premedicated at Various Times | | | | | |
|---|---|---|---|---|---|---|
| | 1 hr. | 3 hr. | 6 hr. | 12 hr. | 24 hr. | 48 hr. |
| Compound of formula (1) | 56.6 | 54.8 | 43.2 | 39.1 | 20.7 | 3.4 |
| Piroxicam | 57.6 | 55.3 | 40.0 | 38.8 | 15.3 | 1.7 |
| Sudoxicam | 49.8 | 52.1 | 39.5 | 31.6 | 10.4 | −2.4 |
| Isoxicam | 54.2 | 54.2 | 45.8 | 36.3 | 19.5 | 1.1 |
| Indomethacin | 49.4 | 57.6 | 29.4 | 18.8 | −3.5 | |
| Diclofenac | 45.9 | 24.7 | 17.6 | 11.8 | −1.2 | |

EXAMPLE 4

The incidence of gastric disorders in rats was tested as follows: Eight-weeks-old male rats of the Wistar strain were used in groups of 5 to 7. After they were fasted for 18 hours or more, a test compound was administered orally. Six hours later, each rat was sacrificed by decapitation. The stomach was removed, filled with 10 ml of physiological saline, and then fixed in 5% formalin. After about 10 minutes, the stomach was incised through the greater curvature and the presence or absence of gastric disorders (in particular, erosion) was examined by visual observation. According to Litchfield-Wilcoxon's method, the dose causing erosion to occur in 50% of the test animals, UD$_{50}$, was calculated on an all-or-none basis. The results thus obtained are shown in Table 4.

TABLE 4

| Test Compound | UD$_{50}$ (mg/kg, p.o.) |
|---|---|
| Compound of formula (1) | 297 |
| Piroxicam | 8.2 |
| Sudoxicam | 11.8 |
| Isoxicam | 250 |
| Indomethacin | 5.4 |
| Diclofenac | 9.2 |
| 6-Methyl-2-pyridyl compound | 5.1 |

EXAMPLE 5

Acute toxicity was tested as follows: Male mice of the ddY strain were used in groups of 5. A test compound was suspended in a 0.2% carboxymethyl cellulose solution and orally administered in a dose of 0.1 ml/10 g of body weight. Thereafter, the animals were observed for 7 days. The LD$_{50}$ value was calculated on the basis of the death rates on the final day. The results thus obtained are shown in Table 5.

TABLE 5

| Test Compound | Dose (mg/kg, p.o.) | Number of Deaths/ Total Number of Test Animals | LD$_{50}$ (mg/kg, p.o.) |
|---|---|---|---|
| Compound of formula (1) | 3,000 | 0/5 | >5,000 |
| | 4,000 | 0/5 | |
| | 5,000 | 0/5 | |
| Piroxicam | 100 | 0/5 | 490 |
| | 200 | 1/5 | |
| | 400 | 1/5 | |
| | 650 | 4/5 | |
| | 800 | 5/5 | |
| Sudoxicam | 200 | 0/5 | 500 |
| | 400 | 2/5 | |
| | 800 | 4/5 | |
| | 1,000 | 5/5 | |
| Isoxicam | 3,000 | 0/5 | 5,000 |
| | 4,000 | 1/5 | |
| | 5,000 | 3/5 | |

EXAMPLE 6

Tablets containing the compound of formula (1) were prepared according to the following recipe:

| Compound of formula (1) | 10 mg |
|---|---|
| Corn starch | 270 mg |
| Polyvinyl pyrrolidone | 15 mg |
| Magnesium stearate | 5 mg |

Using a tablet machine, the above ingredients were blended and compressed into a tablet.

EXAMPLE 7

Capsules containing the compound of formula (1) were prepared according to the following recipe:

| Compound of formula (1) | 10 mg |
|---|---|
| Corn starch | 230 mg |
| Lactose | 50 mg |
| Magnesium stearate | 10 mg |

The above ingredients were blended and enclosed in a hard gelatin shell.

EXAMPLE 8

Suppositories containing the compound of formula (1) were prepared by suspending 20 mg of the finely powdered compound of formula (1) in 5 ml of O.D.O. (triglycerides of medium-chain fatty acids, a product of Nisshin Seiyu Co.) and enclosing the resulting suspension in a soft gelatin shell.

What is claimed is:

1. N-(6-fluoro-2-pyridyl)-3,4-dihydro-2-methyl-4-oxo-2H-1,2-benzothiazine-3-carboxamide 1,1-dioxide.

2. An anti-inflammatory composition comprising N-(6-fluoro-2-pyridyl)-3,4-dihydro-2-methyl-4-oxo-2H-1,2-benzothiazine-3-carboxamide 1,1-dioxide and a pharmaceutical carrier.

* * * * *